United States Patent [19]

Timmerman et al.

[11] Patent Number: 5,837,718
[45] Date of Patent: Nov. 17, 1998

[54] IMIDAZOLE-DERIVATIVES HAVING AGONISTIC OR ANTAGONISTIC ACTIVITY ON THE HISTAMINE H3-RECEPTOR

[75] Inventors: Hendrik Timmerman, Voorschoten; Henderikus Van Der Goot, Hoofddorp, both of Netherlands

[73] Assignee: Seed Capital Investment (SCI) B.V., GA Utrecht, Netherlands

[21] Appl. No.: 476,032

[22] Filed: Jun. 7, 1995

Related U.S. Application Data

[63] Continuation of Ser. No. 108,621, Oct. 6, 1993, abandoned.

[51] Int. Cl.$^6$ ...................... A61K 31/415; C07D 233/60; C07D 233/90; C07D 233/94

[52] U.S. Cl. ......................... 514/341; 514/398; 514/400; 546/278; 548/326.5; 548/329.1; 548/336.1

[58] Field of Search ..................... 514/398, 341, 514/400; 546/278; 548/336.1, 329.1, 326.5

[56] References Cited

U.S. PATENT DOCUMENTS

| | | | |
|---|---|---|---|
| 4,262,125 | 4/1981 | Klaubert | 546/278 |
| 5,047,418 | 9/1991 | Howson | 514/400 |

FOREIGN PATENT DOCUMENTS

| | | | |
|---|---|---|---|
| 0041359 | 12/1981 | European Pat. Off. | C07D 233/64 |
| 0129033 | 12/1984 | European Pat. Off. | G03C 5/54 |
| 0177808 | 4/1986 | European Pat. Off. | C07D 233/64 |
| 0262448 | 4/1988 | European Pat. Off. | C07D 233/64 |
| 2311536 | 12/1976 | France | A61K 31/395 |
| 2052692 | 5/1971 | Germany | C07D 49/36 |
| 2433625 | 1/1975 | Germany | C07D 233/88 |
| 1296544 | 11/1972 | United Kingdom | C07D 49/36 |
| 8707891 | 12/1987 | WIPO | C07D 233/64 |
| 9215567 | 9/1992 | WIPO | |

OTHER PUBLICATIONS

H. Van Der Goot et al., "Isothiourea Analogues of Histamine as Potent Agonists or Antagonists of the Histmine $H_3$–Receptor," Eur. J. Med. Chem., 27, pp. 511–517 (1992).

Comprehensive Medicinal Chemistry, The Rational Design, Mechanistic Study and Therapeutic Application of Chemical Compounds, vol. 3, Pergamon Press, pp. 349–350 (1990).

Journal of Medicinal Chemistry, "Histamin $H_3$ Ligands: Just Pharmacological Tools or Potential Therapeutic Agenst?," Timmerman, vol. 33, No. 1, pp. 4–11, 1990.

*Primary Examiner*—Johann Richter
*Assistant Examiner*—Taofiq A. Soloka
*Attorney, Agent, or Firm*—Webb Ziesenheim Bruening Logsdon Orkin & Hanson, P.C.

[57] ABSTRACT

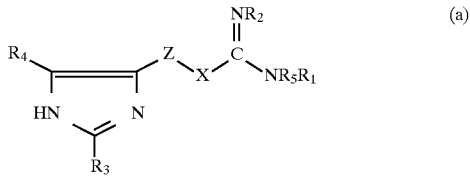

The invention relates to imidazole-derivatives of general formula (a). The invention in particular relates to derivatives having agonistic or antagonistic activity on the histamine $H_3$-receptor. The novel imidazole-derivatives are isothiourea-, guanidine- and amidine-derivatives. The invention further relates to pharmaceutical compositions comprising the novel imidazole-derivatives as well as to methods for preparing the derivatives and for preparing pharmaceutical compositions having antagonistic and agonistic activity on the histamine 3 receptor.

18 Claims, No Drawings

IMIDAZOLE-DERIVATIVES HAVING AGONISTIC OR ANTAGONISTIC ACTIVITY ON THE HISTAMINE H3-RECEPTOR

This application is a continuation-in-part of U.S. patent application Ser. No. 08/108,621, filed Oct. 6, 1993 now abandoned and entitled "IMIDAZOLE-DERIVATIVES HAVING AGONISTIC OR ANTAGONISTIC ACTIVITY ON THE HISTAMINE $H_3$-RECEPTOR".

The invention relates to novel imidazole derivatives. The invention in particular relates to novel imidazole-derivatives having agonistic or antagonistic activity on the histamine $H_3$-receptor. More in particular it relates to isothiourea-, guanidine- and amidine-derivatives. The invention further relates to the synthesis of such compounds, a pharmaceutical composition comprising such compounds or pharmacological acceptable salts thereof, the use of the compounds as agents having biological activity, as agents with agonistic or antagonistic activity of the histamines $H_3$-receptor or for preparing a pharmaceutical composition.

In addition to the already longer known histamine $H_1$- and $H_2$- receptors there is also a third type histamine-receptor present in the human body, the so-called $H_3$-receptor. The $H_3$-receptor is a presynaptic receptor, i.e. it is located on a cell releasing histamine and stimulation of the receptor leads to inhibition of the histamine-release. Furthermore stimulation of the $H_3$- receptor influences also the release of other neurotransmitters, such as e.g. serotonine and acetylcholine. $H_3$-receptors are located in the central and peripheral nervous system, the lung tissue, the intestine and probably also in the spleen, the skin and the gastro-intestinal tract. A number of compounds having an effect on $H_3$-receptors has already been described. For a review see Schwartz et al., Agents and Actions 30, 1/2 (1990) p.13–23.

Chemical compounds can stimulate or inhibit the histamine $H_3$-receptor (Timmerman, J. Med. Chem. 33, p. 4–11 (1990)). Now a group of new imidazole-derivatives showing an agonistic or antagonistic activity on the histamine $H_3$-receptors has been found.

These derivatives are represented by the general formula:

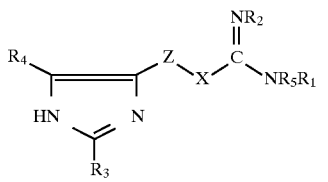
(I)

wherein:

Z is a group of the formula $(CH_2)_m$, wherein m=1–5;
X is S or NH;
$R_1$ is hydrogen, $(C_1-C_3)$alkyl-, aryl$(C_1-C_{10})$ alkyl, aryl or diaryl $(C_1-C_{10})$ alkyl wherein aryl may be substituted with substituents selected from the group consisting of F, Cl, Br, I, $-CH_3$, $-OCH_3$ and $-NO_2$, $(C_5-C_7)$cycloalkyl $(C_1-C_{10})$-, or a group of the formula:

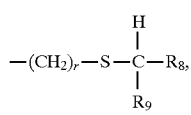

wherein r=1–4, $R_8$ is aryl, aryl$(C_1-C_{10})$alkyl-, $(C_5-C_7)$cycloalkyl- or $(C_5-C_7)$cycloalkyl$(C_1-C_{10})$alkyl-; and
$R_9$ is hydrogen, $(C_1-C_{10})$ alkyl- or aryl;

$R_2$ and $R_5$ are each hydrogen, $(C_1-C_3)$alkyl-, aryl or arylalkyl-; $R_3$ is hydrogen, $(C_1-C_3)$ alkyl, aryl or arylalkyl; and $R_4$ is hydrogen, amino-, nitro-, cyano-, halogen, $(C_1-C_3)$alkyl-, aryl or arylalkyl;

or pharmacologically acceptable salts thereof; with the proviso that a) when X is NH and m=2 or 3, then $R_1$ is not aryl$(C_3-C_4)$ alkyl;
b) when X is NH and m is 4, then $R_1$ is not phenylethyl;
c) when X is NH and m=2, 3 or 4, then $R_1$ is not $(C_1-C_3)$alkyl;
d) when X is S and m=1, 3 or 4, then $R_1$ is not hydrogen or $(C_1-C_3)$alkyl; and
e) when X is S and m=2, $R_1$ is not hydrogen, $(C_1-C_3)$ alkyl or benzyl.

S-[2-(4-imidazolyl)ethyl]isothiourea shows a strong agonistic activity and is therefore preferred as the active ingredient in a pharmaceutical composition having histamine $H_3$-agonistic activity.

Antagonistic activity is in particular shown by compounds of formula I, wherein $R_3$, $R_4$ and $R_5$ are hydrogen; m is 2 or 3, $R_1$ is a group of the formula $-(CH_2)_n R_{10}$, wherein $R_{10}$ is aryl or substituted aryl, $n \geq 1$ and X is S or NH. Preferred compounds are:

S-[2-(imidazol-4-yl)ethyl]-N-(2-phenylethyl)-isothiourea,
N-benzyl-S-[3-(4(5)-imidazolyl)propyl]isothiourea,
S-[3-(4(5)-imidazolyl)propyl]-N-(2-phenylethyl) isothiourea,
S-[3-(4(5)-imidazolyl)propyl]-N-(3-phenylpropyl) isothiourea,
S-[3-(4(5)-imidazolyl)propyl]-N-(4-phenylbutyl) isothiourea,
S-[3-(4(5)-imidazolyl)propyl]-N-(4-chlorobenzyl) isothiourea,
N-cyclohexylmethyl-S-[3-(4(5)-imidazolyl)propyl] isothiourea,
S-[3-(4(5)-imidazoly)propyl]-N-[2-(4-iodophenyl)ethyl]-isothiourea,
N-(4-fluorobenzyl)-S-[3-(4(5)-imidazolyl)propyl]-isothiourea.2HBr
N-[2-(4-chlorophenyl)ethyl]-S-[3-(4(5)imidazolyl)propyl]isothiorea.2HBr
N-(4-bromobenzyl)-S-[3-(4(5)-imidazolyl)propyl] isothiourea.2HBr
N-[2-(4-bromophenyl)ethyl]-S-[3-(4(5)-imidazolyl)propyl] isothiourea.2HBr
N-(4-iodobenzyl)-S-[3-(4(5)-imidazolyl)propyl] isothiourea.2HBr
N-[2-(4-iodophenyl)ethyl]-S-[3-(4(5)-imidazolyl)propyl] isothiourea.2HBr
S-[3-(4(5)-imidazolyl)propyl]-N-(4-methylbenzyl) isothiourea.2HBr
S-[3-(4(5)-imidazolyl)propyl]-N-[2-(4-methylphenyl) ethyl]isothiourea.2HBr
S-[3-(4(5)-imidazolyl)propyl]-N-[2-(4-methoxybenzyl) isothiourea.2HBr
S-[3-(4(5)-imidazolyl)propyl]-N-[2-(4-methoxyphenyl) ethyl)]isothiourea.2HBr
N-(3,4-dichlorobenzyl)-S-[3-(4(5)-imidazolyl)propyl] isothiourea.2HBr
N-benzyl-S-[4-(4(5)-imidazolyl)butyl]isothiourea dipicrate
N-(2-phenylethyl)-S-[4-(4(5)-imidazolyl)butyl]isothiourea dipicrate Other compounds showing strong antagonistic activity are compounds of formula I, wherein $R_3$, $R_4$ and $R_5$ are hydrogen, m is 1, 2 or 3; and $R_1$ is a group of the formula

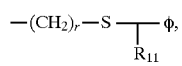

wherein φ is aryl, r is 1, 2 or 3; and $R_{11}$ is hydrogen, $(C_1-C_{10})$ alkyl- or aryl. A preferred compound is N-[2-(benzylthio)ethyl]-S-[3-(imidazol-4-yl)propyl]isothiourea.

Compounds of formula I can in general be synthesized in a for analogous compounds known manner. Favourable methods for synthesizing consist in condensation of a imidazole-compound of the general formula:

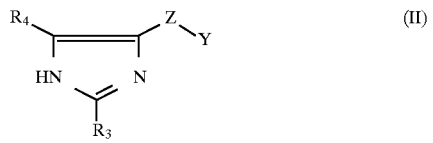

wherein Y represents BR, OH, or O-alkyl, with a thiourea-derivative having the general formula:

or condensation of a imidazole of formula II wherein Y represents $NH_2$, with a isothiourea-derivative having the general formula:

wherein in the formulas III and IV R represents hydrogen, $(C_1-C_{10})$alkyl-, aryl$(C_1-C_{10})$alkyl- or aryl, and $R_{12}$ represents $(C_1-C_{10})$alkyl. As solvents polar solvents are used such as ethanol or propanol. The condensations are carried out at temperatures between room temperature and the boiling point of the solvents for between 30 minutes and 10 hours. Reactions take place in acid environment, e.g. hydrobromic acid, or in neutral environment. The obtained product can be processed in the usual way. It is further possible to convert the obtained compounds of formula I in other compounds of formula I.

The following examples illustrate the synthesis of compounds of the present invention but are never intended to limit the scope thereof.

EXAMPLE 1

Synthesis of N-benzyl-S-[2-(imidazol-4-yl)ethyl] isothiourea dipicrate (VUF 9028).

3.5 gram (13.7 mmol) 4(5)-(2-bromoethyl) imidazole-.HBr and 2.3 gram N-benzylthiourea were refluxed for 60 hours in 30 ml ethanol. The ethanol was evaporated and the product was purified by means of column chromatography, using methanol/ethylacetate as eluent.

Subsequently the solvent was evaporated and the residue dissolved in methanol whereto 10 gram picric acid in methanol was added. After addition of water an oil was formed, which after stirring with water became solid. The solid matter with melting point 166.9°–169.8° C. was subsequently filtrated. The NMR-results of this compound are given in table 1.

EXAMPLE 2

Synthesis of S-[ω-(4(5)-imidazolyl)alkyl]-N-(ω-(substituted)-arylalkyl)isothiourea-derivatives.

Analogous to the preparation method of VUF 9028 from example 1 a number of compounds were synthesized with the formula:

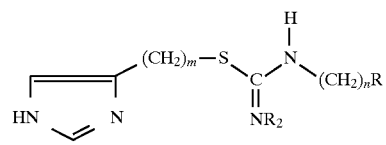

The meaning of n, m and R, the solvent of the condensation reaction and the melting points of the compounds are given in the table below. The NMR-results are given in table 1.

| Compound | $R_2$ | R | n | m | meltpoint | salt | solvent |
|---|---|---|---|---|---|---|---|
| VUF 8397 | H | $C_6H_5$ | 0 | 2 | 174–176° C. | 2HBr | 2-prop. |
| VUF 9029 | H | $C_6H_5$ | 2 | 2 | 177–185° C. | 2HBr | eth. |
| VUF 9030 | H | $C_6H_5$ | 3 | 2 | 152–155° C. | dipicr. | eth. |
| VUF 9031 | H | $C_6H_5$ | 4 | 2 | 136–139° C. | 2HBr | eth. |
| VUF 9051 | $CH_3$ | $C_6H_5$ | 2 | 2 | 152–156° C. | 2HBr | eth. |
| VUF 9107 | H | $C_6H_5$ | 1 | 3 | 155–160° C. | 2HBr | eth. |
| VUF 9151 | H | $C_6H_5$ | 2 | 3 | 178–183° C. | 2HBr | eth. |
| VUF 9152 | H | $C_6H_5$ | 3 | 3 | 177–184° C. | 2HBr | eth. |
| VUF 9153 | H | $4\text{-}ClC_6H_4$ | 1 | 3 | 200–205° C. | 2HBr | eth. |
| VUF 9163 | H | $c\text{-}C_6H_{11}$ | 1 | 3 | 137–153° C. | dipicr. | eth. |
| VUF 4571 | H | $C_6H_5$ | 4 | 3 | 112–134° C. | dipicr. | eth. |
| VUF 4586 | H | $4\text{-}IC_6H_4$* | 2 | 3 | 188–190° C. | 2HBr | 2-prop. |

*Radioactively labeled compound, e.g. for use as a tracer

EXAMPLE 3

Synthesis of N-[2-(imidazol-4-yl)ethyl]-N'-phenyl guanidine dipicrate (VUF 9006).

Step 1:
Synthesis of S-ethyl-N-phenylisothiourea.

4 gram N-phenylisothiourea (33 mmol) and 5 ml ethyl bromide were refluxed for 10 hours in ethanol. Again 5 ml ethyl bromide was added. The reaction course was followed by thin layer chromatography (ethylacetate/petroleumether 3:7). Subsequently the solvent was evaporated and the residue crystallised from ethanol/ethylacetate.

Step 2:
15 mmol histamine.2HCl was added to 30 mmol sodium ethanolate in ethanol (prepared by dissolving 30 mmol sodium in ethanol). Subsequently it was refluxed for one half hour, after which the mixture was cooled in ice and the formed NaCl was filtrated.

To the filtrate 15 mmol S-ethyl-N-phenylisothiourea was added. Next the reaction mixture was refluxed for 35 hours (control with layer chromatography (ethyl acetate/petroleumether 1:1, saturated with ammonia)). Subsequently the solvent was evaporated and the residue dissolved in methanol. 35 mmol picric acid were added. The product was seperated by the addition of water and was subsequently crystallised from methanol/water. The melting point was 235°–238° C.

Analogous to the synthesis of VUF 9006 N-[2-(imidazol-4-yl)ethyl]-N'-phenyl-ethylguanidine dipicrate (VUF 9007; meltingpoint 196°–198° C.) was prepared. The NMR-results are given in table 1.

EXAMPLE 4

Synthesis of N-[ω-arylalkylthio)alkyl]-S-[ω-(imidazol-4-yl)alkyl]isothiourea- and -guanidine-derivatives.

Analogous to example 1 compounds were synthesized having the formula:

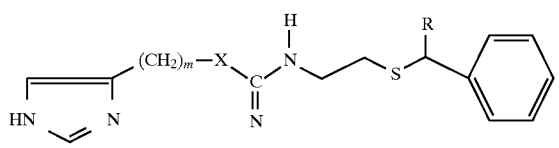

The meaning of the symbols m, X and R, the solvent of the condensation reaction and the melting points of the compounds are given in the table below. The NMR-results are given in table 1.

| Compounds | m | X | R | melting point | salt | solvent |
|---|---|---|---|---|---|---|
| VUF 8404 | 2 | S | H | 233–235° C. | 2HBr | 2-prop. |
| VUF 8405 | 3 | NH | H | 145–148° C. | dipicr. | ethanol |
| VUF 8409 | 2 | S | $C_6H_5$ | 106–109° C. | dipicr. | ethanol |
| VUF 8414 | 3 | S | H | 126–133° C. | dipicr. | ethanol |

EXAMPLE 5

Synthesis of N-alkyl-S-[ω-(4-imidazolyl)alkyl]isothiourea- and -guanidine-derivatives.

Analogous to example 1 compounds were synthesized having the formula:

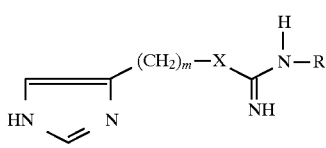

The meaning of the symbols m, X and R, the solvent of the condensation reaction and the melting points of the compounds are given in the table below. The NMR-results are given in table 1.

| Compound | m | X | R | melting point | salt | solvent |
|---|---|---|---|---|---|---|
| VUF 8325 | 2 | S | H | 210–212° C. | 2HBr | eth. |
| VUF 83100 | 2 | NH | H | 222–223° C. | 2HCl | eth. |
| VUF 8621 | 2 | S | $CH_3$ | 180–181° C. | 2HBr | water |

EXAMPLE 6

Synthesis of N-phenylalkyl-S-[ω-(4(5)imidazolyl)alkyl] isothiourea.2HBr (general procedure)

Compounds of the general formula:

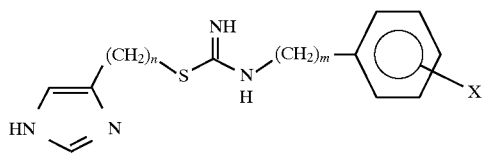

were prepared as follows.

X mmole 4(5)-(ω-bromoalkylimidazole).HBr and Y mmole N-(ω-phenylalkyl)isothiourea in absolute alcohol were added to a r.b. flask, provided with a cooler. The mixture was refluxed for 4 days. After that, the reaction mixture was evaporated and processed. The processing comprises flash chromatography (eluent: MeOH/ethyl acetate) followed by recrystallization from a suitable solvent. This yielded a white solid. According to this method the following compounds were synthesized with the parameters "X", "Y", solvent, yield, efficiency, melting point and NMR-results indicated.

1. N-(4-fluorobenzyl)-S-[3-(4(5)-imidazolyl)propyl] isothiourea.2HBr (VUF 4650)

X=20 mmole (5.40 g)
Y=25 mmole (4.60 g)
solvent: isopropanol
yield: 1.75 g (19.8%)
melting point: 176.0°–187.0° C.
NMR-results: $^1$H-NMR (D$_2$O): δ 1.86–1.96 ppm (m, 2H, C-CH$_2$-C), 2.72–2.90 ppm (m, 2H, im-CH$_2$), 3.13–3.28 ppm (m, 2H, S-CH$_2$), 4.59 ppm (s, 2H, fenyl-CH$_2$), 7.09–7.42 ppm (m, 6H, fenyl-H en im-H$_6$), 8.60 ppm (s, 1H, im-H$_2$).

2. N-[2-(4-chlorophenyl)ethyl]-S-[3-4(5)imidazolyl) propyl]isothiorea.2HBr (VUF 4657)

X=20 mmole (5.40 g)
Y=25 mmole (5.37 g)
Prior to recrystallization the crude compound was refluxed in 250 ml isopropanol and filtrated to remove organic contaminants.
solvent: methanol
yield after recrystallization from methanol: 2.58 g (27%)
melting point: 205.2° C.
NMR-results: $^1$H-NMR (D$_2$O): δ 1.65–1.98 ppm–2.13 ppm (m, 2H, C-CH$_2$-C), 2.70 ppm (t, 2H, im-CH$_2$), 2.82–3.10 ppm (m, 4H, N-CH$_2$+fenyl-CH$_2$), 3.70 ppm (t, 2H, S-CH$_2$), 7.10–7.40 ppm (m, 5H, fenyl-H en im-H$_5$), 8.60 ppm (s, 1H, im-H$_2$)

3. N-(4-bromobenzyl)-S-[3-(4(5)-imidazolyl)propyl] isothiourea.2HBr (VUF 4651)

X=14.1 mmole (3.80 g)
Y=15.6 mmole (3.80 g)
Prior to recrystallization the crude compound was refluxed in 250 ml isopropanol and filtrated to remove organic contaminants.
solvent: methanol
yield after recrystallization from methanol: 0.91 g (12.5%)
melting point: 198.2°–201.5° C.
NMR-results: $^1$H-NMR (D$_2$O): δ 2.00 ppm (m, 2H, C-CH$_2$-C), 2.80 ppm (m, 2H, im-CH$_2$), 3.15 ppm (t, 2H, S-CH$_2$), 4.55 ppm (a, 2H, Ar-CH$_2$), 7.20 ppm (m, 3H, fenyl-H en im-H$_5$), 7.55 ppm (d, 2H, fenyl-H),8.55 ppm (s, 1H, im-H$_2$).

4. N-[2-(4-bromophenyl)ethyl]-S-[3-(4(5)-imidazolyl) propyl] isothiourea.2HBr (VUF 4598)

X=10 mmole (2.70 g)
Y=13.3 mmole (3.44 g)
Prior to recrystallization the crude compound was refluxed in 250 ml isopropanol and filtrated to remove organic contaminants.
solvent: methanol
yield after recrystallization from methanol: 1.63 g (23.3%)
melting point: 202.2°–203.5° C.
NMR-results: $^1$H NMR (D$_2$O): δ 1.62–1.85 ppm (m, 2H, C-CH$_2$-C), 2.70 ppm (m, 2H, im-CH$_2$), 2.80–3.10 ppm (m, 4H, N-CH$_2$+Ar-CH$_2$), 3.70 ppm (t, 2H, S-CH$_2$), 7.10–7.50 ppm (2d+s, 5H, fenyl-H en im-H$_5$), 8.60 ppm (s, 1H, im-H$_2$).

5. N-(4-iodobenzyl)-S-[3-(4(5)-imidazolyl)propyl] isothiourea.2HBr (VUF 4652).

X=9.0 mmole (2.7 g)
Y=12 mmole (3.5 g)
solvent: isopropanol
yield:0.79 g (18%)
melting point: 190°–192.7° C.

NMR-results: $^1$H-NMR (DMSO-d$_6$): δ 1.99 ppm (m, 2H, C-CH$_2$-C), 2.84 ppm (t, 2H, im-CH$_2$), 3.17 ppm (t, 2H, S-CH$_2$), 4.54 ppm (s,2H, Ar-CH$_2$), 7.05–7.18 ppm (m, 2H, fenyl-H), 7.19 ppm (d, 1H, im-H$_5$), 7.70–7.85 ppm (m, 2H, fenyl-H), 8.46 ppm (d, 1H, im-H$_2$).

6. N-[2-(4-iodophenyl)ethyl]-S-[3-(4(5)-imidazolyl)propyl]isothiourea.2HBr (VUF 4586)
X=5.0 mmole (1.53 g)
Y=5.0 mmole (1.53 g)
solvent: ethanol
yield: 0.95 g (33%)
melting point: 171.8°–174.0° C.
NMR-results: $^1$-NMR (DMSO-d$_6$); δ 1.89 ppm (m, 2H, C-CH$_2$-C), 2.74 ppm (t, 2H, Ar-CH$_2$), 2.83 ppm (t, 2H, im-CH$_2$), 3.24 ppm (t, 2H, N-CH$_2$), 3.57 ppm (t, 2H, S-CH$_2$), 7.05–7.20 ppm (m, 2H, fenyl-H), 7.50 ppm (s, 1H, im-H$_5$), 7.60–7.75 ppm (m, 2H, fenyl-H), 9.03 ppm (s, 1H, im-H$_2$), 9.25 ppm (br s, 2H, N-H), 9.68 ppm (br s, 1H, NH), 14.05 ppm (br s, 2H, im-NH).

7. S-[3-(4(5)-imidazolyl)propyl]-N-(4-methylbenzyl) isothiourea.2HBr (VUF 4653)
X=20 mmole (5.40 g)
Y=25 mmole (4.53 g)
solvent: ethanol/ethylacetate
yield: 1.37 g (15.2%)
melting point: 1.92°–198.7° C.
NMR-results: $^1$-NMR (D$_2$O): δ 1.95–2.15 ppm (m, 2H, C-CH$_2$-C), 2.45 ppm (s, 3H, CH$_3$), 2.85 ppm (t, 2H, im-CH$_2$), 3.18 ppm (t, 2H, S-CH$_2$), 4.57 ppm (s, 2H, Ar-CH$_2$), 7.22 ppm (s, 1H, im-H$_5$), 7.30 ppm (s, 4H, fenyl-H), 8.56 ppm (s, 1H, im-H$_2$).

8. S-[3-(4(5)-imidazolyl)propyl]-N-[2-(4-methylphenyl)ethyl]isothiourea.2HBr (VUF 4658)
X=20 mmole (5.40 g)
Y=25 mmole (4.86 g)
solvent: methanol
yield: 1.57 g (17%)
melting point: 211.2°–214.5° C.
NMR-results: $^1$H-NMR (D$_2$O): δ 1.75–1.95 ppm (m, 2H, C-CH$_2$-C), 2.20 ppm (s, 3H, CH$_3$), 2.75 ppm (t, 2H, im-CH$_2$), 2.82–3.10 ppm (m, 4H, N-CH$_2$+Ar-CH$_2$), 3.70 ppm (t, 2H, S-CH$_2$), 7.10–7.25 ppm (m, 5H, fenyl-H+im-H$_5$), 8.57 ppm (s, 1H, im-H$_2$).

9. S-[3(4(5)-imidazolyl)propyl]-N-[2-(4-methoxybenzyl) isothiourea.2HBr (VUF 4654)
X=20 mmole (5.40 g)
Y=20 mmole (3.93 g)
solvent: ethanol
yield: 2.69 g (29%)
melting point: 181.0°–184.0° C.
NMR-results: $^1$H-NMR (D$_2$O): δ 1.90–2.15 ppm (m, 2H, C-CH$_2$-C), 2.82 ppm (t, 2H, CH$_2$-im), 3.18 ppm (t, 2H, S-CH$_2$), 3.70 ppm (s, SH, OCH$_3$), 4.65 ppm (s, 2H, Ar-CH$_2$), 6.90–7.45 ppm (2d+s, 5H, fenyl-H+im-H$_5$), 8.60 ppm (s, 1H, im-H$_2$).

10. S-[3-(4(5)-imidazolyl)propyl]-N-[2(4-methoxyphenyl) ethyl)]isothiourea.2HBr (VUF 4659)
X=20 mmole (4.21 g)
Y=20 mmole (5.40 g)
solvent: methanol
yield: 2.84 g (30%)
melting point: 171.8°–174.2° C.
NMR-results: $^1$H-NMR (D$_2$O): δ 1.65–1.90 ppm (m,2H, C-CH$_2$-C), 2.67 ppm (t, 2H, CH$_2$-im), 2.80–3.05 ppm (m, 4H, N-CH$_2$+Ar-CH$_2$), 3.65 ppm (s, 2H, S-CH$_2$), 3.70 ppm (s, 3H, OCH$_3$), 6.80–7.25 ppm (2d+s, 5H, fenyl-H+im-H$_5$), 8.55 ppm (s, 1H, im-H$_2$).

11. N-(3,4-dichlorobenzyl)-S-[3-(4(5)-imidazolyl)propyl] isothiourea.2HBr (VUF 4656).
X=20 mmole (4.60 g)
Y=25 mmole (5.93 g)
solvent: methanol
yield: 1.51 g (15%)
melting point: 213.9°–214.4° C.
NMR-results: $^1$H-NMR (D$_2$O): δ 1.87–2.08 ppm (m, 2H, C-CH$_2$-C), 2.78 ppm (t, 2H, im-CH$_2$), 3.15 ppm (t, 2H, S-CH$_2$), 4.60 ppm (s, 2H, Ar-CH$_2$), 7.12–7.80 ppm (m, H, fenyl-H en im-H$_5$), 8.55 ppm (s, 1H, im-H$_2$).

12. N-benzyl-S-[4-(4(5)-imidazolyl)butyl]isothiourea dipicrate (VUF 4661)
X=19.3 mmole (5.48 g)
Y=19.3 mmole (3.22 g)
It was not possible to recrystallize the endproduct as a diHBr salt. Therefore a dipicrate was prepared. For this the product was dissolved in 100 ml methanol and 2 eq. picric acid in 50 ml methanol were added dropwise while stiffing. Subsequently the product was precipitated by slowly adding water. A yellow solid crystallized which was filtrated.
yield: 2.10 g (14.6%)
melting point: 146.8°–149.6° C.
NMR-results: $^1$H-NMR (DMSO-d$_6$): δ 1.65 ppm (m, 4H, C-CH$_2$-CH$_2$-C),2.65 ppm (t, 2H, im-CH$_2$), 3.20 ppm (t, 2H, S-CH$_2$), 4.58 ppm (d, 2H, fenyl-CH$_2$), 7.30–7.50 ppm (m, 6H, fenyl-H+im-H$_5$), 8.60 ppm (s, 4H, picraat-H), 9.00 ppm (s, 1H, im-H$_2$), 9.30 ppm (br s, 2H, =NH$_2$), 10.00 ppm (t,1H, NH), 14.10 ppm (m, 2H, im-NH).

13. N-(2-phenylethyl)-S-[4-(4(5)-imidazolyl)butyl] isothiourea dipicrate (VUF 4662)
X=19.3 mmole (5.48 g)
Y=19.3 mmole (3.49 g)
Analogous to compound 12 a dipicrate was prepared.
yield: 3.78 g (25.7%)
melting point: 160.6°–167.0° C.
NMR results: $^1$H-NMR (DMSO-d6): δ 1.62 ppm (m,4H, C-CH$_2$-CH$_2$-C),2.65 ppm(t, 2H, Ar-CH$_2$), 2.85 ppm (t, 2H, im-CH$_2$), 3.17 ppm (m, 2H, N-CH$_2$), 3.55 ppm (m, 2H, S-CH$_2$), 7.30 ppm (m, 5H, fenyl-H), 7.42 ppm (s, 1H, im-H$_5$), 8.60 ppm (s, 4H, picraat-H), 9.00 ppm (s, 1H, im-H$_2$), 9.20 ppm (br s, 2H, N=H), 9.62 ppm (t, 1H, NH), 14.05 ppm (m, 2H, im-NH).

The following table shows the above described compounds in summary and lists their antagonistic activity.

| X | n | m | pA$_2$ | VUF code |
|---|---|---|---|---|
| H | 4 | 1 | 8.72 | 4661 |
| H | 4 | 2 | 8.13 | 4662 |
| 4-F | 3 | 1 | 9.38 | 4650 |
| 4-Br | 3 | 1 | 9.77 | 4651 |
| 4-I | 3 | 1 | 9.21 | 4652 |
| 4-CH$_3$ | 3 | 1 | 9.36 | 4653 |
| 4-OCH$_3$ | 3 | 1 | 9.39 | 4654 |
| 3,4-Cl$_2$ | 3 | 1 | 8.96 | 4656 |
| 4-Cl | 3 | 2 | 9.2 | 4657 |
| 4-I | 3 | 2 | 8.7 | 4586 |
| 4-CH$_3$ | 3 | 2 | 8.4 | 4658 |
| 4-Br | 3 | 2 | 9.0 | 4598 |
| 4-OCH$_3$ | 3 | 2 | 8.3 | 4659 |

TABLE 1

NMR-results of the compounds mentioned in the description.

COMPOUNDS
AGONISTS

VUF8325

| | | | | |
|---|---|---|---|---|
| 3.06 | ppm | triplet | J = 7.0 Hz | 2H |
| 3.56 | ppm | triplet | J = 7.0 Hz | 2H |
| 7.61 | ppm | singlet | | 1H |
| 9.01–9.27 | ppm | multiplet | | 5H |

VUF8621

| | | | | |
|---|---|---|---|---|
| 2.93 | ppm | singlet | | 3H |
| 3.07 | ppm | triplet | J = 6.8 Hz | 2H |
| 3.59 | ppm | triplet | J = 6.8 Hz | 2H |
| 7.60 | ppm | singlet | | 1H |
| 9.11 | ppm | doublet | J = 1.3 Hz | 1H |

ANTAGONISTS

VUF9028

| | | | | |
|---|---|---|---|---|
| 3.06 | ppm | triplet | J = 6.9 | 2H |
| 3.54 | ppm | triplet | J = 6.9 | 2H |
| 4.58 | ppm | singlet | | 2H |
| 7.29–7.49 | ppm | multiplet | | 6H |
| 7.52 | ppm | singlet | | 4H |
| 8.62 | ppm | singlet | | 1H |
| 9.08 | ppm | doublet | J = 1.3 Hz | 1H |

VUF9029

| | | | | |
|---|---|---|---|---|
| 2.90 | ppm | triplet | J = 7.5 Hz | 2H |
| 3.00 | ppm | triplet | J = 7.0 Hz | 2H |
| 3.50–3.69 | ppm | multiplet | | 4H |
| 7.21–7.35 | ppm | multiplet | | 5H |
| 7.58 | ppm | singlet | | 1H |
| 9.16 | ppm | doublet | J = 1.3 Hz | 1H |

VUF9030

| | | | | |
|---|---|---|---|---|
| 1.86 | ppm | quintet | J = 7.4 Hz | 2H |
| 2.62 | ppm | triplet | J = 7.4 Hz | 2H |
| 3.05 | ppm | triplet | J = 6.9 Hz | 2H |
| 3.24–3.38 | ppm | multiplet | | 2H |
| 3.51 | ppm | triplet | J = 6.9 Hz | 2H |
| 7.16–7.39 | ppm | multiplet | | 5H |
| 7.53 | ppm | singlet | | 1H |
| 8.61 | ppm | singlet | | 4H |
| 9.06 | ppm | doublet | J = 1.3 Hz | 1H |

VUF9031

| | | | | |
|---|---|---|---|---|
| 1.45–1.71 | ppm | multiplet | | 4H |
| 2.60 | ppm | triplet | | 2H |
| 3.05 | ppm | triplet | J = 6.8 Hz | 2H |
| 3.30–3.45 | ppm | multiplet | | 2H |
| 3.60 | ppm | triplet | J = 6.8 Hz | 2H |
| 7.13–7.46 | ppm | multiplet | | 5H |
| 7.60 | ppm | singlet | | 1H |
| 9.13 | ppm | doublet | J = 1.4 Hz | 1H |

VUF9051

| | | | | |
|---|---|---|---|---|
| 2.80–3.06 | ppm | multiplet | | 4H |
| 3.50–3.68 | ppm | multiplet | | 4H |
| 7.18–7.40 | ppm | multiplet | | 5H |
| 7.57 | ppm | singlet | | 1H |
| 9.09 | ppm | singlet | | 1H |

VUF9006

| | | | | |
|---|---|---|---|---|
| 2.90 | ppm | triplet | J = 6.3 Hz | 2H |
| 3.51 | ppm | triplet | J = 6.3 Hz | 2H |
| 7.14–7.50 | ppm | multiplet | | 5H |
| 7.69–7.86 | ppm | multiplet | | 2H |
| 8.59 | ppm | singlet | | 4H |
| 8.97 | ppm | singlet | | 1H |

VUF9007

| | | | | |
|---|---|---|---|---|
| 2.74–2.92 | ppm | multiplet | | 4H |
| 3.32–3.51 | ppm | multiplet | | 4H |
| 7.18–7.50 | ppm | multiplet | | 6H |
| 8.63 | ppm | singlet | | 4H |
| 9.05 | ppm | doublet | | 1H |

VUF8404

| | | | | |
|---|---|---|---|---|
| 2.66 | ppm | triplet | J = 6.3 Hz | 2H |
| 3.06 | ppm | triplet | J = 6.3 Hz | 2H |
| 3.40–3.72 | ppm | multiplet | | 4H |
| 3.81 | ppm | singlet | | 2H |
| 7.28 | ppm | singlet | | 5H |
| 7.58 | ppm | singlet | | 1H |
| 9.07 | ppm | doublet | J = 0.8 Hz | 1H |

VUF8405

| | | | | |
|---|---|---|---|---|
| 1.64 | ppm | quintet | J = 7.2 Hz | 2H |
| 2.38–2.84 | ppm | multiplet | | 4H |
| 3.06–3.56 | ppm | multiplet | | 4H |
| 3.80 | ppm | singlet | | 2H |
| 7.26–7.44 | ppm | multiplet | | 6H |
| 8.60 | ppm | singlet | | 4H |
| 9.02 | ppm | singlet | | 1H |

VUF8409

| | | | | |
|---|---|---|---|---|
| 2.56 | ppm | triplet | J = 6.8 Hz | 2H |
| 3.03 | ppm | triplet | J = 6.8 Hz | 2H |
| 3.26–3.70 | ppm | multiplet | | 4H |
| 5.40 | ppm | singlet | | 1H |
| 7.10–7.56 | ppm | multiplet | | 11H |
| 8.60 | ppm | singlet | | 4H |
| 9.02 | ppm | singlet | | 1H |

VUF8414

| | | | | |
|---|---|---|---|---|
| 1.94 | ppm | quintet | J = 6.8 Hz | 2H |
| 2.60–2.94 | ppm | multiplet | | 4H |
| 3.20 | ppm | triplet | J = 6.8 Hz | 2H |
| 3.30–3.68 | ppm | multiplet | | 2H |
| 3.78 | ppm | singlet | | 2H |
| 7.28–7.42 | ppm | multiplet | | 6H |
| 8.60 | ppm | singlet | | 4H |
| 9.00 | ppm | doublet | J = 1.0 Hz | 1H |

VUF9107

| | | | | |
|---|---|---|---|---|
| 1.86–2.05 | ppm | multiplet | | 2H |
| 2.76 | ppm | triplet | J = 7.5 Hz | 2H |
| 3.20–3.51 | ppm | multiplet | | 7H |
| 4.60 | ppm | singlet | | 2H |
| 7.26–7.52 | ppm | multiplet | | 6H |
| 9.01 | ppm | doublet | J = 1.3 Hz | 1H |

VUF9151

| | | | | |
|---|---|---|---|---|
| 1.81–1.98 | ppm | multiplet | | 2H |
| 2.73 | ppm | triplet | J = 7.5 Hz | 2H |
| 2.89 | ppm | triplet | J = 7.0 Hz | 2H |
| 3.22 | ppm | triplet | J = 7.0 Hz | 2H |
| 3.34 | ppm | singlet | | 6H |
| 3.52–3.68 | ppm | multiplet | | 2H |
| 7.20–7.40 | ppm | multiplet | | 5H |
| 7.48 | ppm | singlet | | 1H |
| 9.02 | ppm | doublet | J = 1.3 Hz | 1H |

VUF9152

| | | | | |
|---|---|---|---|---|
| 1.78–2.06 | ppm | multiplet | J = 7.6 Hz | 4H |
| 2.64 | ppm | triplet | J = 7.3 Hz | 2H |
| 2.77 | ppm | triplet | | 2H |
| 3.19–3.50 | ppm | multiplet | | 10H |
| 7.18–7.40 | ppm | multiplet | | 5H |
| 7.49 | ppm | singlet | | 1H |
| 9.01 | ppm | doublet | J = 1.3 Hz | 1H |

VUF9153

| | | | | |
|---|---|---|---|---|
| 1.86–2.06 | ppm | multiplet | J = 7.2 Hz | 2H |
| 2.77 | ppm | triplet | | 2H |
| 3.22–3.49 | ppm | multiplet | | 6H |
| 4.60 | ppm | singlet | | 2H |
| 7.32–7.58 | ppm | multiplet | | 6H |
| 9.04 | ppm | doublet | J = 1.3 Hz | 1H |

TABLE 1-continued

NMR-results of the compounds mentioned in the description.

VUF9163

| | | | | |
|---|---|---|---|---|
| 0.80–1.77 | ppm | multiplet | | 11H |
| 1.86–2.03 | ppm | multiplet | | 2H |
| 2.74 | ppm | triplet | J = 7.0 Hz | 2H |
| 3.08–3.25 | ppm | multiplet | | 4H |
| 3.35 | ppm | singlet | | 10H |
| 7.46 | ppm | singlet | | 1H |
| 8.49 | ppm | singlet | | 4H |
| 8.98 | ppm | doublet | J = 1.3 Hz | 1H |

VUF4571

| | | | | |
|---|---|---|---|---|
| 1.47–1.70 | ppm | multiplet | | 4H |
| 1.84–2.03 | ppm | multiplet | | 2H |
| 2.42–2.66 | ppm | multiplet | | 50H |
| 2.74 | ppm | triplet | J = 7.2 Hz | 2H |
| 3.19 | ppm | triplet | J = 7.2 Hz | 2H |
| 3.26–3.38 | ppm | multiplet | | 2H |
| 3.46 | ppm | multiplet | | 10H |
| 7.11–7.35 | ppm | multiplet | | 5H |
| 7.47 | ppm | singlet | | 1H |
| 8.59 | ppm | singlet | | 4H |

VUF4586

| | | | | |
|---|---|---|---|---|
| 1.89 | ppm | multiplet | | 2H |
| 2.74 | ppm | triplet | J = 7.2 Hz | 2H |
| 2.83 | ppm | triplet | J = 7.0 Hz | 2H |
| 3.24 | ppm | multiplet | | 2H |
| 3.57 | ppm | multiplet | J = 7.2 Hz | 2H |
| 7.05–7.20 | ppm | multiplet | | 2H |
| 7.60–7.75 | ppm | multiplet | | 2H |
| 7.50 | ppm | singlet | | 1H |
| 9.03 | ppm | singlet | | 1H |

Pharmacological experiments

The agonistics and antagonistics activities on the $H_3$-receptor of the various compounds were determined compared to histamine. The test methods used therefor are described in Van der Werf et al., Agents and Actions 20, 3/4 (1987) p. 239–243 and Menkveld et al., European Journal of Pharmacology, 186 (1990) p. 343–347.

The results of the experiments are given in the tables below. $pD_2$ is the negative logarithm of the concentration of the test compound at which 50% agonistic activity was measured. $pA_2$ is the negative logarithm of the concentration of the test compound at which the concentration of the agonist had to be doubled to obtain the same effect as obtained when the antagonist was absent.

Pharmaceutical compositions, comprising compounds of formula I as defined in claim 19 as the active ingredient for therapeutically influencing the human and animal histaminergic system have the form of powders, suspensions, solutions, sprays, emulsions, unguents or creams and can be used for local application, intranasal, rectal, vaginal and also for oral or parenteral (intravenous, intradermal, intramusculer, intrathecal etc.) administration. Such compositions can be prepared by combining (i.e. by mixing, dissolving etc.) of the active compound of formula I in the form of a free acid or salt with pharmaceutically acceptable excipients with neutral character (such as aquous or non-aquous solvents, stabilizers, emulsifiers, detergents, additives), and further if necessary colouring agents and flavouring agents. The concentration of the active ingredient in a pharmaceutical composition can vary between 0.1% and 100%, depending on the nature of the influence and the method of administration. The dose of the active ingredient that is administered can further be varied between 0.1 mg and 100 mg per kg bodyweight.

TABLE 2

Antagonistic activity

| Compound | $pA_2$ | test method |
|---|---|---|
| VUF 8397 | 7.0 | rat cortex |
| VUF 9028 | 7.8 | ileum guinea pig |
| VUF 9029 | 8.0 | ileum guinea pig |
| VUF 9030 | 7.6 | ileum guinea pig |
| VUF 9031 | 7.7 | ileum guinea pig |
| VUF 9051 | 7.8 | ileum guinea pig |
| VUF 9006 | 5.8 | ileum guinea pig |
| VUF 9007 | 6.3 | ileum guinea pig |
| VUF 8404 | 7.4 | ileum guinea pig |
| VUF 8405 | 7.9 | ileum guinea pig |
| VUF 8409 | 6.6 | ileum guinea pig |
| VUF 8414 | 8.6 | ileum guinea pig |
| VUF 9107 | 8.8 | ileum guinea pig |
| VUF 9151 | 8.8 | ileum guinea pig |
| VUF 9152 | 8.3 | ileum guinea pig |
| VUF 9153 | 9.9 | ileum guinea pig |
| VUF 9163 | 8.8 | ileum guinea pig |
| VUF 4571 | 8.4 | ileum guinea pig |
| VUF 4586 | 9.2 | ileum guinea pig |

TABLE 3

Agonistic activity

| Compound | $pD_2$ | test method |
|---|---|---|
| VUF 8325 | 9.3 | rat cortex |
| VUF 8325 | 8.1 | ileum guinea pig |
| VUF 83100 | 7.4 | rat cortex |
| VUF 8621 | 7.3 | ileum guinea pig |

We claim:

1. A compound of the formula:

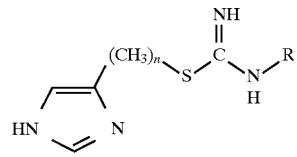

wherein, n is 3, and R is selected from the group consisting of (4-fluorobenzyl), [2-(4-chlorophenyl)ethyl], (4-bromobenzyl), [2-(4-bromophenyl)ethyl], (4-iodobenzyl), [2-(4-iodophenyl)ethyl], [2-(4-methoxybenzyl)], [2(4-methoxyphenyl)ethyl] and (3,4-dichlorobenzyl) and a salt, selected from the group consisting of 2HBr and dipicrate.

2. An imidazole derivative wherein said derivative is N-cyclohexylmethyl-S-[3-(4(5)-imidazoyl)propyl]isothiourea.

3. An imidazole derivative wherein said derivative is N-[2-(benzylthio)ethyl]-S-[3-(imidazoyl-4-yl)propyl]isothiourea.

4. A pharmaceutical composition comprising a suitable excipient and as an active ingredient the compound of claim 3 or a pharmacologically acceptable salt thereof, wherein said active ingredient is between 0.1% to 100% of said pharmaceutical composition.

5. A method for preparing the compound of claim 1 by condensation of 4(5)-(ω-bromoalkylimidazole)·HBr and N-(ω-phenylalkyl)isothiourea.

6. A pharmaceutical composition comprising a suitable excipient and as an active agent a compound as recited in claim 1 wherein said active ingredient is between 0% and 100% of said pharmaceutical composition.

7. A pharmaceutical composition comprising a suitable excipient and as an active ingredient the compound of claim 3 or a pharmacologically acceptable salt thereof, wherein said active ingredient is between 0.1% to 100% of said pharmaceutical composition.

8. A method of inducing agonistic or antagonistic activity of histamine $H_3$-receptors in a patient in need thereof which comprises administering to said patient a pharmaceutical composition having agonistic or antagonistic activity on the histamine $H_3$-receptor, wherein said pharmaceutical composition is the composition of claim 4.

9. A method of inducing agonistic or antagonistic activity of histamine $H_3$-receptors in a patient in need thereof which comprises administering to said patient a pharmaceutical composition having agonistic or antagonistic activity on the histamine $H_3$-receptor, wherein said pharmaceutical composition is the composition of claim 7.

10. The complex as claimed in claim 1, wherein the compound is N-(4-fluorobenzyl)-S-[ω-(4(5)imidazolyl)propyl]isothiourea and the salt is 2HBr.

11. The complex as claimed in claim 1, wherein the compound is N-[2-(4-chlorophenyl)ethyl]-S-[ω-(4(5)imidazolyl)propyl]isothiourea and the salt is 2HBr.

12. The complex as claimed in claim 1, wherein the compound is N-(4-bromobenzyl)-S-[ω-(4(5)imidazolyl)propyl]isothiourea and the salt is 2HBr.

13. The complex as claimed in claim 1, wherein the compound in N-[2-(4-bromophenyl)ethyl]-S-[ω-(4(5)imidazolyl)propyl]isothiourea and the salt is 2HBr.

14. The complex as claimed in claim 1, wherein the compound is N-(4-iodobenzyl)-S-[ω-(4(5)imidazolyl)propyl]isothiourea and the salt is 2HBr.

15. The complex as claimed in claim 1, wherein the compound is N-[2-(4-iodophenyl)ethyl]-S-[ω-(4(5)imidazolyl)propyl]isothiourea and the salt is 2HBr.

16. The complex as claimed in claim 1, wherein the compound is N-[2-(4-methoxybenzyl)]-S-[ω-(4(5)imidazolyl)propyl]isothiourea and the salt is 2HBr.

17. The complex as claimed in claim 1, wherein the compound is N-[2-(4-methoxyphenyl)ethyl]-S-[ω-(4(5)imidazolyl)propyl]isothiourea and the salt is 2HBr.

18. The complex as claimed in claim 1, wherein the compound is N-(3,4-dichlorobenzyl)-S-[ω-(4(5)imidazolyl)propyl]isothiourea and the salt is 2HBr.

* * * * *

UNITED STATES PATENT AND TRADEMARK OFFICE
CERTIFICATE OF CORRECTION

PATENT NO. : 5,837,718
DATED : November 17, 1998
INVENTOR(S) : Hendrik Timmerman and Henderikus Van Der Goot It is certified that error appears in the above-identified patent and that said Letters Patent is hereby corrected as shown below:

Title Page, insert:
--[30] Foreign Application Priority Data
Feb. 27, 1991 [NE] Netherlands........ 9100365
Oct. 22, 1991 [NE] Netherlands........ 9101764
Feb. 27, 1992 [NL] Netherlands........ PCT/NL92/00041--.

Title Page, under OTHER PUBLICATIONS, last reference: "Agents" should read --Agents--.

Column 1 Line 19 "of the histamines" should read --on the histamines--.

Column 2 Line 38 "imidazoly" should read --imidazolyl--.

Column 2 Line 42 after "(4/5)" insert hyphen (-).

Column 2 Line 43 "isothiorea" sould read --isothiourea--.

Column 4 Line 30, footnote: after "tracer" insert --molecule--.

Column 4 Line 51 between "with" and "layer" insert --thin--.

Column 5 Line 48 after "(4(5)" insert hyphen (-).

Column 6 Line 16 after "(4(5)" insert hyphen (-).

Column 6 Line 17 "isothiorea" should read --isothiourea--.

UNITED STATES PATENT AND TRADEMARK OFFICE
CERTIFICATE OF CORRECTION

PATENT NO. : 5,837,718
DATED : November 17, 1998
INVENTOR(S) : Hendrik Timmerman and Henderikus Van Der Goot It is certified that error appears in the above-identified patent and that said Letters Patent is hereby corrected as shown below:

Column 7 Line 13 "$^1$-NMR" should read --$^1$H-NMR--.

Column 7 Line 27 "$^1$-NMR" should read --$^1$H-NMR--.

Column 7 Line 53 "SH" should read --3H--.

Column 8 Line 18 "endproduct" should read --end product--.

Column 8 Line 22 "stiffing" should read --stirring--.

Column 8 Line 42 "(DMSO-d6)" should read --(DMSO-$d_6$)--.

Column 10 Line 61 after "multiplet" delete --J=7.2 Hz--.

Column 10 Line 62 after "triplet" insert --J=7.2 Hz--.

Column 11 Line 59 "aquous" should read --aqueous--.

Column 11 Lines 59-60 "non-aquous" should read --non-aqueous--.

Claim 1 Column 12, in the formula: "($CH_3$)" should read --($CH_2$)--.

Claim 2 Column 12 Line 52 "imidazoyl" should read --imidazolyl--.

Claim 3 Column 12 Line 55 "imidazoyl" should read --imidazolyl--.

UNITED STATES PATENT AND TRADEMARK OFFICE
CERTIFICATE OF CORRECTION

PATENT NO.   : 5,837,718
DATED        : November 17, 1998
INVENTOR(S)  : Hendrik Timmerman and Henderikus Van Der Goot It is certified that error appears in the above-identified patent and that said Letters Patent is hereby corrected as shown below:

Claim 4 Column 12 Lines 57-58 "of claim 3" should read
--of claim 2--.

Claim 6 Column 12 Line 66 "0%" should read --0.1%--.

Signed and Sealed this

Sixth Day of July, 1999

Q. TODD DICKINSON

*Attest:*

*Attesting Officer*     Acting Commissioner of Patents and Trademarks